Nov. 18, 1975 T. T. KIRSCH Plant Pat. 3,805
LILY PLANT (YELLOW JEWEL)
Filed Oct. 15, 1974
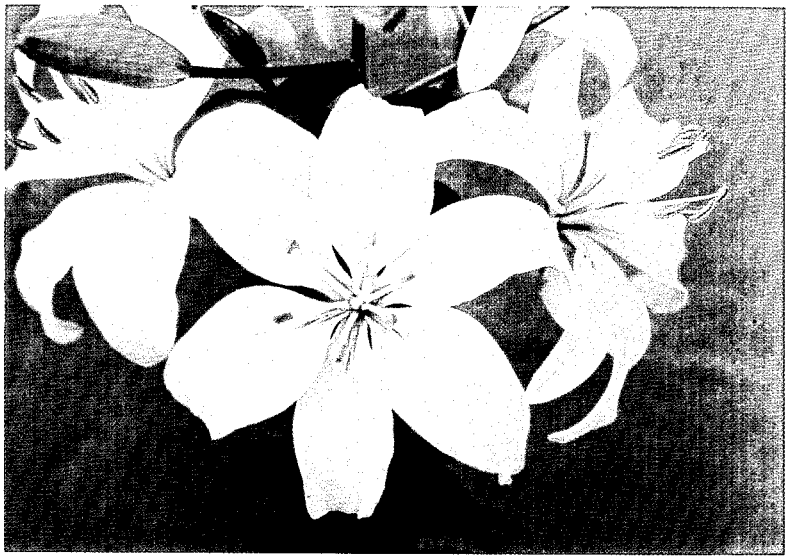
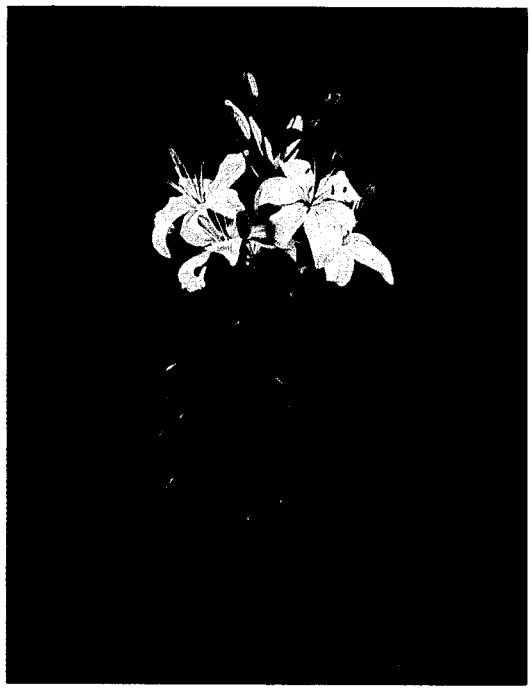

United States Patent

Plant Pat. 3,805

Patented Nov. 18, 1975

3,805

LILY PLANT

Ted T. Kirsch, Sitkum Rte., Box 142,
Myrtle Point, Oreg. 97458

Filed Oct. 15, 1974, Ser. No. 514,796
Int. Cl. A01h 5/00

U.S. Cl. Plt.—68 1 Claim

ABSTRACT OF THE DISCLOSURE

A new variety of lily plant, of the chalice-type of Asiatic hybrid, particularly distinguished by the light yellow and gold coloring of the flowers which are borne in a raceme arrangement that terminates in an umbel cluster on strong upright stems.

BACKGROUND OF THE INVENTION

My new variety of lily plant originated as a seedling of unknown parentage and was discovered by me in 1971 while growing among a planting of random seedling bulblets in a test plot on my property at Arcata, Calif. The lovely flowers of this plant were noted by me to be of an unusual coloring and shape, quite different than any other yellow lily of the same type, and my subsequent asexual propagation of this plant at Arcata, Calif., by means of scales and through several successive generations has shown that its distinctive characteristics are firmly fixed and hold true from generation to generation. This new variety of lily plant is now being produced for commercial exploitation by means of tissue culture and scales at Arcata, Calif.

DESCRIPTION OF THE DRAWING

My new variety of lily plant is illustrated by the accompanying photographic drawing in full color which shows a face view of a fully opened flower and a view of an entire plant shown at about midway of its blooming cycle, the colors shown being as nearly true as can be reasonably obtained by conventional photographic procedures. The true color is shown by the painted swatch affixed to the drawing.

DESCRIPTION OF THE NEW PLANT

The following is a detailed description of my new variety of lily plant with color designations according to the R.H.S. Colour Chart of the Royal Horticultural Society of London, England.

THE PLANT

Origin: Seedling.
Parentage: Unknown.
Classification: Asiatic hybrid. Chalice-type.
Form: Tall single stem from each bulb.
Height: One to three feet, depending upon the size (age) of the bulb.
Growth: Sturdy and upright with excellent strength.
Cane size: Stems grow from ¼ inch in diameter at height of about one foot to 1 inch in diameter for plants reaching a height of about three feet.
Foliage: Quantity—abundant.
*Size of leaf.*—Stem leaves—From 2 to 4 inches long and from ½ to 1¼ inches wide. Leaves at flower cluster—3 in number, 1½ to 2¾ inches long and 1 to 1¾ inches wide.
*Shape of leaf.*—Lanceolate.
*Texture.*—Leathery. Aspect: Smooth.
Stem bulbils:
*Occurrence.*—Produced occasionally in leaf axils.
*Size.*—⅛ inch to ¼ inch in diameter.

*Color.*—Reddish green depending on exposure to sunlight.
Stem bulblets (under ground):
*Occurrence.*—From 2 to 6 on each healthy normal plant at digging time.
*Size.*—¼ inch to 1 inch in diameter.
*Color.*—White.
Bulbs:
*Size.*—From 1 inch to 3 inches in diameter.
*Color.*—White.

THE BUD

Form: Elongate-oblong with obtuse apex.
Size: Average, 2 to 3 inches long and ½ to ¾ inch in diameter.
Opening: Normal, with tertiary and secondary buds opening successively.
Color: Greenish yellow when sepals first divide and petals begin to unfurl.
Pedicel: Strong and generally upright. Angled about 30° from vertical.
*Length.*—3 to 4 inches.
*Number of buds.*—1 to 3 on each pedicel.

THE FLOWER

Blooming habit: Annually, blooming profusely in June or early July.
Size: Medium, averaging about 5½ inches diameter and about 1 inch in depth.
Borne: From large bulbs the inflorescence has a raceme arrangement for the first 2 to 6 pedicels (each with 2 or 3 buds) and then at the top breaks into an umbel cluster of 2 to 8 pedicels with one bloom on each pedicel. Small bulbs often flower an umbel cluster only of one bloom on each pedicel. The size of the bulb and its cultural care will determine the number of blooms and buds to be found on any given inflorescence. From large bulbs this lily may have 6 to 8 blooms open at one time, one on each pedicel and 2 or 3 open on the top umbel cluster.
Shape: Generally flat with uniformly spaced petals in star arrangement and outer third of petal length slightly recurved.
Petalage: Normal—3 sepals and 3 petals.
*Form.*—Elliptical with obtuse apex, prominent nectariferous grooves and a center furrow bisecting each petal longitudinally. Edges entire.
*Color.*—Upper side—Upon opening, RHS 6A (Yellow Group) with a dark green nectariferous groove having light green margins fading into light greenish yellow in base portion of petal. Occasionally petals will have two or three dark "pepper spots." After being open to sunlight one day, the general color of the petals darkens to RHS 7B (Yellow Group). Under side—Light yellow, near RHS 6A. The flower color may vary, either lighter or darker, according to the soil and climate in which the plant is grown.
*Papillae.*—None.
*Texture.*—Leathery.
*Appearance.*—Velvety.
Fragrance: Not noticeable.
Discoloration: Color becames somewhat darker as blossom matures.
Effect of weather: Flower is generally not affected by wet weather but flower ages as temperature rises.
Lasting quality: Excellent. 3 to 6 weeks on plant, depending on size of bulb and temperature, and 10 days to 2 weeks as a cut flower.
Persistence: The flower tends to hang on and dry.

REPRODUCTIVE ORGANS

Stamens:

*Anthers.*—6 in number. Arrangement: Orderly around style. Length: About ½ inch.

Filaments: About 2 inches long.

*Color.*—Pale Yellow.

Pistils:

*Number.*—One.

*Style.*—About 2 inches long.

*Stigma.*—Very light green in color.

Ovary: Contained in a seed pod, about 1½ inches long and 1 inch in diameter, having 6 rows of seeds of the usual shape.

My new variety of lily plant most nearly resembles the variety Early of Rochester (unpatented) and is distinguished from that variety by having wider leaves and by being of a lighter yellow in flower color and having blooms that are less cup-shaped with petals and sepals that are much wider at their base. Also, the new variety differs from Earl of Rochester in that flowers of the new plant have shorter filaments and the style is of about the same length as the filaments. The new variety is sturdier than Earl of Rochester and the inflorescence is more rigid and formal appearing.

The claim:

1. A new and distinct variety of Asiatic hybrid lily plant substantially as herein shown and described characterized by the color, form and arrangement of its bright yellow flowers, by its profuse production of flower buds which bloom progressively to provide an extended blooming period, and by the long lasting quality of the blooms on the plant and as cut flowers.

No references cited.

ROBERT E. BAGWILL, Primary Examiner